United States Patent [19]

Talalla et al.

[11] Patent Number: 4,633,889
[45] Date of Patent: Jan. 6, 1987

[54] STIMULATION OF CAUDA-EQUINA SPINAL NERVES

[76] Inventors: Andrew Talalla, Oriole Lodge, 195 Lake Street, Grimsby, Ontario L3M 4M1, Canada; Leo A. Bullara, 704 E. Kirkwall Rd., Glendora, Calif. 91740

[21] Appl. No.: 681,121

[22] Filed: Dec. 12, 1984

[51] Int. Cl.⁴ ............................................. A61N 1/04
[52] U.S. Cl. .................................... 128/784; 128/642
[58] Field of Search ............ 128/419 R, 419 P, 419 C, 128/419 E, 419 G, 642, 784, 786

[56] References Cited

U.S. PATENT DOCUMENTS

| | | | |
|---|---|---|---|
| 3,664,347 | 5/1972 | Harmjanz | 128/786 |
| 3,769,984 | 11/1973 | Muench | 128/419 P |
| 3,957,036 | 5/1976 | Normann | 128/642 |
| 4,030,508 | 6/1977 | Thalen | 128/786 |
| 4,105,037 | 8/1978 | Richter et al. | 128/419 P |
| 4,301,805 | 11/1981 | Peers-Trevarton | 128/419 P |
| 4,440,178 | 4/1984 | Bussard et al. | 128/784 |
| 4,458,695 | 7/1984 | Peers-Trevarton | 128/786 |
| 4,481,953 | 11/1984 | Gold et al. | 128/786 |

Primary Examiner—William E. Kamm
Assistant Examiner—Mitchell J. Shein
Attorney, Agent, or Firm—Christie, Parker & Hale

[57] ABSTRACT

A nerve-stimulating electrode assembly for installation within or adjacent the lower end of the dura mater to enable regaining of at least partial control over lower-body functions directed by nerves emerging from the end of the spinal cord. In one form, the electrode assembly has an internal passage enabling injection of fluids, whereby electrical stimulation, chemical treatment, or both forms of therapy may be used either intra- or extradurally.

10 Claims, 8 Drawing Figures

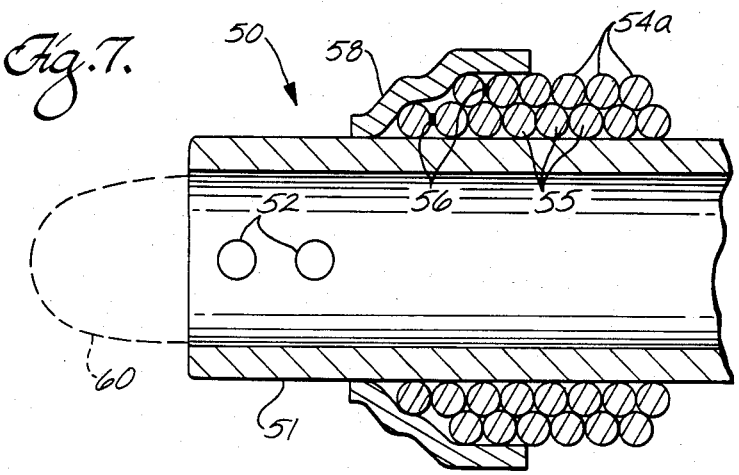
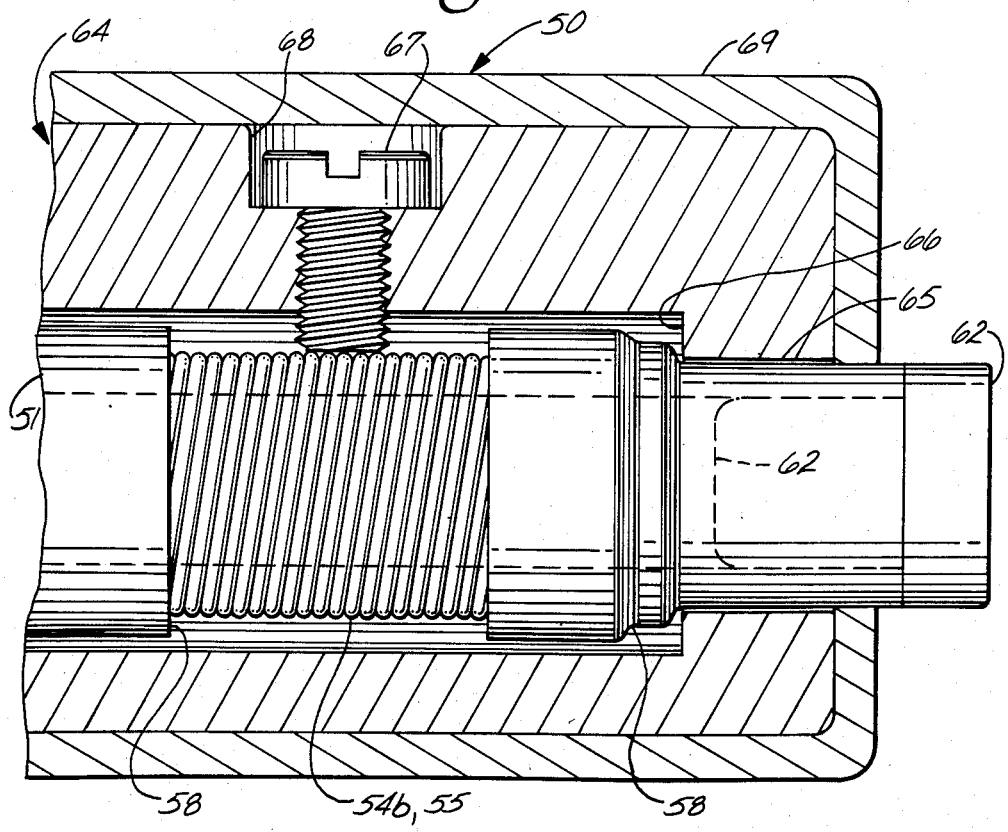

4,633,889

STIMULATION OF CAUDA-EQUINA SPINAL NERVES

BACKGROUND OF THE INVENTION

Stimulation of selected nerves in the human nervous system by electrical signals is a known technique in assisting accident or disease victims who have lost normal neuromuscular control. The resulting paralysis is often seen in spinal-injury victims who lose voluntary control of the entire lower body. Injury or disease of this type interrupts the normal control mechanisms of the brain and spinal cord, leading to malfunctioning of motor and sensory systems, as well as other systems under nerve control below the point of injury or disease.

The nerve bundles and fibers below (toward the lower body) the injury site typically remain in good condition, but are nonfunctional due to the "open circuit" in the spinal cord. In theory, it should be possible to stimulate specific nerves below the point of injury or disease, and hence to activate the muscles, or other organs or systems controlled by those nerves, by applying electrical signals to electrodes surgically implanted on nerves emerging from the intact lower spinal cord. In practice, however, this goal is difficult to achieve because the spinal cord is a highly protected structure within the body, and conventional electrode-implantation surgical procedures are difficult, complex, and lengthy, thus presenting a relatively high degree of risk and trauma to the patient.

The spinal cord is surrounded by a tough tubular membrane serving as a protective sheath and called the dura mater (or simply "dura"). The dura is in turn protected and surrounded by the vertebrae which form the spinal column or backbone. The hollow interiors of the vertebrae form a vertebral canal through which the dura and cord extend, and the tissue- and vein-filled annular space between the wall of this canal and the dura is called the epidural space.

The space between the spinal cord (the surface of which is covered by a more delicate membrane called the pia mater) and the interior of the dura is filled with cerebrospinal fluid ("CSF") which is enclosed by the third of the cord-protecting meninges called the arachnoid. The dura extends substantially below the lower end or conus medullaris of the spinal cord. The lower end of the dura is filled with CSF and occupied by the lumbar and sacral nerves (each of which has a dorsal sensory root and a ventral motor or muscle-controlling root) and a bundle of smaller nerve fibers, all collectively called the cauda equina. These nerves are of great importance in that they control leg movement, as well as a number of lower body functions such as urination.

One way of reaching those nerves to enable artificial electrical stimulation involves a major surgical operation to expose the sacral nerves where they emerge from the dura. Electrodes can then be secured to the appropriate nerve bundles (depending on the function to be controlled), and the implanted electrodes are then energized by electronic devices which may be either internal or external to the patient's body. This kind of surgery is lengthy and difficult, and involves significant risk and recovery problems for the patient.

The electrode system of this invention overcomes many of these problems by enabling a greatly simplified surgical installation procedure. The new electrode is designed for introduction into the lower end of the dura beneath the conus of the spinal cord to float in the intrathecal (or "within the sheath") space loosely occupied by the sacral roots and other nerves of the cauda equina. Installation of the electrode is of little more complexity and risk than that presented by a conventional lumbar-puncture spinal tap for withdrawing a diagnostic sample of CSF from the subarachnoid space around the cauda equina. The electrode system is also useful in an extradural position to stimulate selected levels of nerves of the cauda equina through the dura.

SUMMARY OF THE INVENTION

This invention relates to an electrode assembly and installation procedure having the objective of enabling paralysis victims to regain partial control over lower-body functions. The electrode assembly has a winding of multiple conductors, portions of which are uninsulated and exposed to form multiple stimulating electrodes. The output electrodes are inserted adjacent or into the dura beneath the conus of the spinal cord by a surgical procedure which is far simpler and safer than the extensive operation needed to enable extradural installation of electrodes on the lower spinal nerves. Radially enlarged spacers on the electrode assembly are provided to avoid direct contact of the output electrodes with the intradural nerves. Stimulating signals from the electrodes are conveyed to the nerves by volume conduction either through the CSF in the dura chamber enclosing the CSF and lower spinal nerves, or from an extradurally positioned electrode assembly through body fluids, the dura wall, and the CSF.

In one form, the electrode assembly includes a hollow tubular core through which drugs or other treatment fluids can be injected into or adjacent the dura. This form of treatment enables differential and selective blocking of nerve conduction in the lowermost spinal nerves. In a chronically implanted system, fluid can be supplied from an implanted chamber such as an Ommaya reservoir.

BRIEF DESCRIPTION OF THE DRAWINGS

FIG. 7 is a sectional elevation of an output-electrode assembly; and

FIG. 8 is a sectional elevation of the input-electrode end of the assembly shown in FIG. 7.

DETAILED DESCRIPTION OF THE PREFERRED EMBODIMENTS

Figure 1:
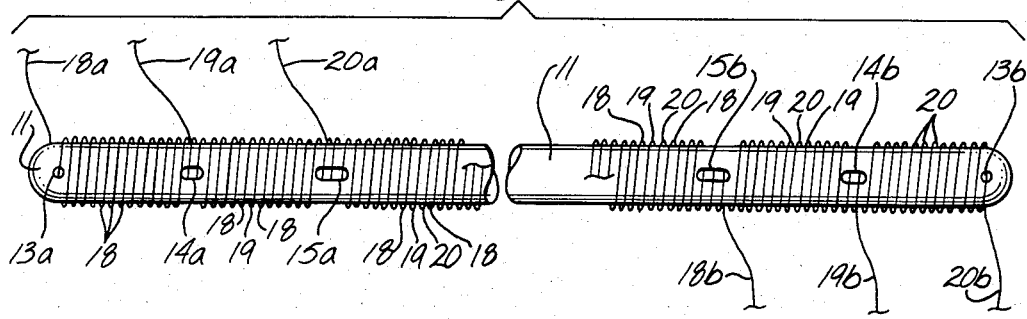
FIG. 1 is a side view of a core and wire windings as used in an electrode assembly of this invention.

An electrode assembly 10 suitable for use in the practice of this invention is shown in FIGS. 1-5. The assembly includes a slender elongated inner core 11 made of a flexible plastic material such as monofilament Teflon plastic. The core is normally solid in cross section, but may be a hollow tube if a passage is desired to enable injection of a fluid medication, or withdrawal of a CSF (spinal fluid) sample after the electrode assembly is implanted.

Core 11 is preferably quite small in diameter (circular cross-sectional dimensions in the range of 0.35 to 0.50 millimeters are typical), and about 30 to 35 centimeters in length to extend from within the lower end of the dura to a connecting cable on an implantable electronic stimulating-signal generator (not shown) in the patient's back. Small circular holes 13a and 13b are formed through the core adjacent its opposite ends, and a second pair of oval-shaped openings 14a and 14b are spaced about 10 to 15 mm inwardly (away from the core ends) from holes 13a and 13b respectively. A third pair of oval-shaped openings 15a and 15b are similarly spaced about 10 to 15 mm inwardly from openings 14a and 14b respectively.

Electrode assembly 10 may have any desired number of separate electrodes, but is typically made in bipolar or tripolar form. As illustrated, the assembly is tripolar, thus providing three separate spaced-apart electrode surfaces which can be separately and independently energized. As explained below, the electrodes are formed by uninsulated portions of three elongated electrically conductive wires 18, 19 and 20 which are closely wrapped along the core in a specific sequence.

Before being wrapped on the core, wires 18–20 are about 3 meters in length, and are preferably made of pure iridium, but a platinum-10% iridium alloy is also suitable. The wire diameter is about 0.075 mm, and each wire has a Teflon-plastic insulating sleeve or jacket of about 0.025 mm wall thickness. After being wound on the core, the ends of each wire are stripped of insulation for a length of about 5 cm, depending on the desired electrode length.

Figure 2:
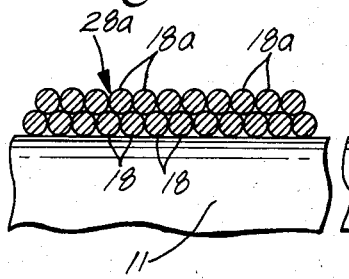
FIG. 2 is an enlarged partial cross section of a portion of the core which carries a single-conductor winding.

One end of first wire 18 is passed through hole 13a to leave a free end 18a extending from the core, and the wire is wrapped around the core to form a locking or anchoring wrap. The wire is then spirally wound around the core between holes 13a and 14a in side-by-side single-layer turns as shown in FIG. 2. Preferably, a conventional coil-winding machine is used to maintain a constant light tension on all wires during construction of the electrode assembly.

Figure 3:
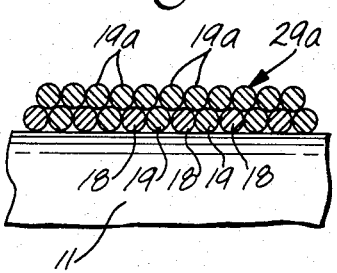
FIG. 3 is an enlarged partial cross section of a portion of the core which carries a winding of two separate conductors.
Figure 4:
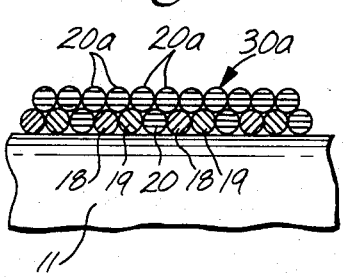
FIG. 4 is an enlarged partial cross section of a portion of a winding of three separate conductors.

Upon reaching and passing through hole 14a, further winding of first wire 18 is interrupted until the end of second wire 19 is passed through hole 14a to form an anchoring wrap, and to leave a free and 19a extending from the core. Wires 18 and 19 are then wrapped side-by-side along the length of the core between holes 14a and 15a as shown in FIG. 3. The turns are closely spaced alternate windings or wraps of the first and second conductive wires.

Upon reaching and passing through elongated hole 15a, further winding of the first and second wires is interrupted until the end of third wire 20 is passed through hole 15a to provide a locking or anchoring wrap, and to leave a free end 20a extending from the core. Winding of the three wires is then continued in side-by-side close-wound spiral fashion (FIG. 4) along the major length of the core between holes 15a and 15b.

As the three-wire single-layer coil reaches hole 15b, a locking wrap of first wire 18 is made through the hole to leave a free end 18b extending from the core. Winding of wires 19 and 20 is then continued to hole 14b where a terminating wrap of wire 19 is formed, leaving a free end 19b. Finally, third wire 20 is coiled in close-wound spiral wraps in the space between holes 14b and 13b to be locked in an anchoring wrap through hole 13b and around the core, leaving a free end 20b.

The extending free ends of wires 18, 19 and 20 at opposite ends of the core are then stripped of insulation for a length of about 5 cm (depending on the electrode area which is desired). Stripped free end 18a is then close wound (FIG. 2) over the first layer of wire 18b for, say, 10 to 15 turns from hole 13a toward hole 14a. Any excess length is snipped off, and the last two turns are spot-welded to anchor the wire end. Similarly, stripped free end 19a is close wound over the first layer of insulated wires between holes 14a and 15a (FIG. 3), and stripped free end 20a is close wound inwardly (away from the distal tip of the core) on the core from hole 15a (FIG. 4) with both free ends terminating in a pair of spot-welded turns.

The extending free ends 18b, 19b, and 20b of the wires are similarly stripped, and then terminated by wrapping over the underlying single layer of insulated wire to form three spaced-apart outer windings of bare wire. These six uninsulated outer windings (three at each end of the core) are the electrodes of the electrode assembly as further discussed below.

Figure 5:
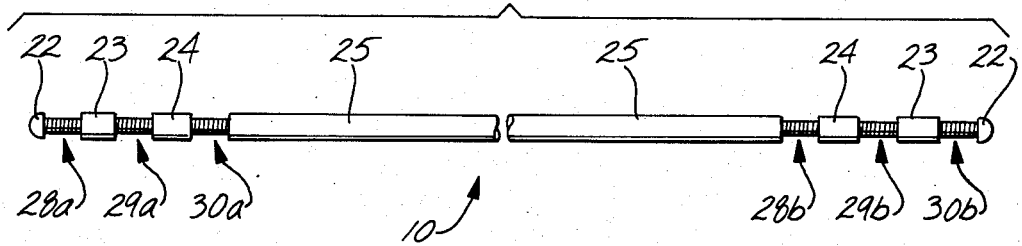
FIG. 5 is a side view of the complete electrode assembly.

When the winding operation is complete, an insulating plastic material (a medical-grade Type 382 silicone elastomer is suitable) is molded around the wire-covered core over holes 13, 14 and 15 to form cylindrical or annular enclosures surrounding portions of the wires as shown in FIG. 5. The material molded at the opposite ends of core 11 forms softly rounded tips 22 which cover and seal holes 13a and 13b and the associated wire ends. The material molded over holes 14 and 15 forms longitudinally spaced-apart cylindrical spacers 23 and 24 at opposite ends of the core. The entire central part of the core is covered with the plastic material to form an elongated central insulating spacer 25 which is spaced apart at its opposite ends from the adjacent spacers to expose the innermost electrodes.

As shown in FIG. 5, tips 22 and spacers 23–25 are substantially larger in outside diameter than the outside diameter of the wire turns around the core. For example, the exposed wire turns between the tips and several spacers typically have an outside diameter in the range of about 0.50 to 0.65 mm, whereas the tips and spacers have outside diameters which are double or more that of the coiled wires, for example about 1.2 mm. The exposed wires are thus recessed well below the outer surface of the tips and spacers.

As will be recalled from the winding sequence, the surface of first wire 18 is uninsulated and exposed as it extends between tip 22 and spacer 23 at the left end of the assembly shown in FIG. 5, and between spacers at the right end of the cores 24 and 25, thereby forming electrodes 28a and 28b adjacent opposite ends of the core. Similarly, the uninsulated ends of second wire 19 form electrodes 29a and 29b between the two pairs of spacers 23 and 24, and the uninsulated ends of third wire 20 form electrodes 30a and 30b between spacers 24 and 25 at the left core end, and between tip 22 and spacer 23 at the right core end.

When the electrode assembly is installed as described below, electrodes 28a, 29a and 30a are within the lower end of the dura to be surrounded by CSF and the nerves of the cauda equina. These output electrodes are thus the delivery or stimulating electrical surfaces which are positioned intrathecally within the dura. Input electrodes 28b, 29b and 30b are external to the spinal cord and can be conducted percutaneously to the outside of the body for short-term hard-wire stimulation, or positioned within the body for connection to an implanted radio-frequency-coupled biostimulator.

Figure 6:
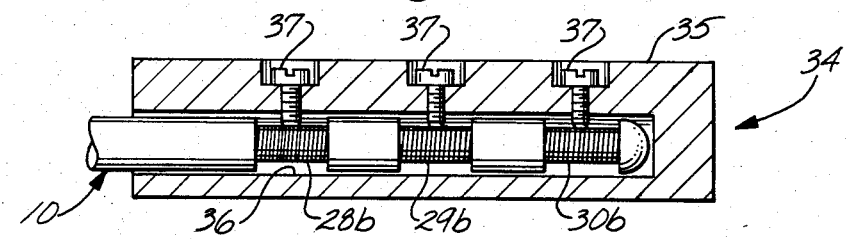
FIG. 6 is a sectional elevation of an input end of the electrode assembly as fitted within a connector assembly.

Connection to the input electrodes can be made in a variety of ways, and a typical convenient connector assembly 34 is shown in FIG. 6. Assembly 34 includes a small acrylic-plastic block 35 having a bore 36 which snugly receives the input end of electrode assembly 10. Three very small (e.g. 0-72 or 0-90) stainless-steel screws 37 are countersunk in the side surface of the block to contact input electrodes 28b, 29b and 30b respectively, thus providing convenient terminals to which leads from the stimulating-signal generator can be connected.

Electrode assembly 10 is longitudinally stiff, but has resiliency and flexibility in a lateral or sideways direction. These properties enable the assembly to be inserted through the bore of a conventional Touhy needle (not shown) which can be inserted into the patient's body by a neurosurgeon. A Touhy needle is either straight or somewhat curved, and is hollow to define a continuous passage or lumen between its ends. The sharp end of the needle is beveled, and has a laterally directed passage outlet such that any flexible solid member passed through the lumen emerges adjacent the needle point in a direction away from the central longitudinal axis of the needle.

As discussed above, the lower end of the dura beneath the conus or lower end of the spinal cord is a CSF-filled chamber containing the sacral roots and other nerves of the cauda equina, and extending between the first lumbar and third sacral vertebral segments. Using only a local anesthetic, the neurosurgeon makes a lumbar puncture with the Touhy needle to penetrate through the dura below the conus into this chamber. This procedure is very similar to a conventional spinal tap, and involves low patient risk and trauma as compared to the major laminectomy surgery needed to expose the spinal nerves outside the dura for installation of clamped electrodes.

With the Touhy needle so installed, output-electrode end of electrode assembly 10 is introduced into and fed through the needle lumen until electrodes 28a–30a are within the dura. The lumen outlet is oriented downwardly to direct the electrodes toward the lower closed end of the dura, while remaining well clear of the conus of the spinal cord. The relatively slender and flexible nerve filaments comprising the cauda equina are easily displaced by the advancing inner end of the electrode assembly.

The exact positioning of the output electrodes within the lower end of the dura will depend on the function to be stimulated. As discussed above, electrical stimulation of different portions of the nerves within the lower end of the dura, and different signal levels, wave forms, and frequencies, can enable restoration of bladder, bowel, sexual, and lower-limb functions. The neurosurgeon has freedom to adjust the position of the output electrodes while applying stimulating signals to determine a placement which produces the desired response in the conscious and only locally anesthetized patient. When proper electrode placement is achieved, the Touhy needle is withdrawn over the outer end of the electrode assembly, and connection of the stimulating-signal source (whether external or implanted) is completed.

An important feature of the invention is the use of CSF within the dura as a transmission medium for electrical-charge injection from the output electrodes to the target nerves. The recessed placement of the electrodes between the enlarged spacers prevents undesired direct contact of the electrodes with nerve surfaces, and enables more uniform stimulation of multiple nerve fibers by volume conduction through the CSF. The longitudinal stiffness of the electrode assembly assures that the initial placement of the output electrodes with respect to the target nerves will be maintained during body movement or stimulation of adjacent muscles.

While the invention has thus far been described in terms of intradural placement, the electrode assembly can also be inserted (using the Touhy needle procedure described above) adjacent the outer surface of the lower end of the dura which contains the cauda equina. Charge injection is then achieved from the electrodes through the extradural body fluids and dura wall to the intradural CSF and nerve surfaces.

A hollow-core alternative embodiment of the invention is shown as an electrode assembly 50 in FIGS. 7 and 8 which show the output and input ends of the assembly respectively. Assembly 50 has a hollow tubular core 51 which is preferably a Teflon-plastic tube with an inside or bore diameter of about 0.010 inch, and a wall thickness of about 0.003 inch. The tube itself is open ended, and additional outlet holes 52 are cut through the sidewall at the outlet or distal end to insure continued fluid delivery even though the end of the tube becomes blocked (for example, by surrounding tissue).

Assembly 50 can be made with any desired number of electrodes (five or more can be accommodated if desired), but is shown in FIGS. 7 and 8 with only a single output electrode 54a and associated input electrode 54b. As described above, these electrodes are formed by the overwrapped bared ends of a wire 55, the insulated part of which is close wound in a single layer between the core ends. In this embodiment, anchoring wire openings through the core sidewall are omitted, and the wire is secured to the core by spot welding the last few turns together as shown at 56.

When the wire-winding and electrode-forming step is complete, the windings apart from the electrodes can be covered with silicone plastic as already described, or this protective and spacing function can be achieved by shrinking over the windings sections of heat-shrink tubing of Teflon plastic (or an equivalent body-compatible material) to form spacers 58.

During installation of assembly 50 through a Touhy needle, core 51 is preferably stiffened by insertion of a conventional slender stainless-steel stylet in the bore of the core. A tip 60 (shown in phantom line in FIG. 7) of the stylet is tapered or rounded to ease insertion of the distal end of the assembly. If inserted intradurally, the outer end of the core is closed with a silicone-plastic stopper 62 immediately after withdrawal of the stylet to avoid loss of CSF through the core. The stopper is of course removed if the core is subsequently connected to either an external or implanted fluid supply.

Assembly 50 is completed by installation of a connector assembly 64 which is generally similar to connector 34, but has a passage 65 to receive the outer end of core 51 as shown in FIG. 8. A shoulder 66 at the inner end of passage 65 abuts the end of outermost spacer 58 to index the input electrode beneath a contact screw 67 threaded into connector block 68. Preferably, the connector assembly is covered with a snug-fitting silicone-rubber boot 69 after the electrode assembly is implanted and the electrical connections are completed.

As with assembly 10, the distal end of electrode assembly 50 can be implanted within the dura, or alongside the outer surface of the dura at the level of the target nerves of the cauda equina. In either case, the charge of the stimulating signal is injected through CSF surrounding the cauda equina within the dura.

Use of multiple electrodes enables the selection of different stimulating-signal protocols which are important in regaining control over lower-body functions. The surface area of the individual electrodes described above is typically in the range of 0.01 to 0.03 square centimeters, and the preferred activated-iridium material of these electrodes enables high levels of charge injection without dissolution of the electrode metal. The desired number and size of electrodes can be easily adjusted during assembly.

A feature of the hollow fluid-conducting assembly described above is that it permits either serial or simultaneous use of both chemical therapy and application of electrical stimulating signals. As a result of the relatively safe installation and implantation of the new electrode assembly, it is hoped that paralysis victims may be assisted in regaining exercise and limited use of the legs, control of such vital functions as bladder and sphinter muscles to enable urination, and other functions which are lost as a result of spinal injuries.

What is claimed is:

1. A nerve-stimulating electrode assembly for delivering stimulating signals through body fluid to spinal nerves within the lower end of the vertebral column, comprising:
    an elongated core;
    a first spiral-wound coil of insulated wire on the core between the core ends, the ends of the wire being uninsulated and wound over the respective ends of the coil to form a pair of first electrodes at opposite ends of the core; and
    means for enabling charge injection through a body fluid to a group of nerves, while deterring direct electrode contact with a nerve surface; said enabling means comprising a plurality of insulating spacers on the core on opposite sides of each electrode, said spacers being larger in outside dimension than said electrodes, whereby said electrodes are recessed between said spacers.

2. The assembly defined in claim 1 wherein the core is a hollow tube with an open distal end.

3. The assembly defined in claim 1, and further comprising at least one further insulated wire spiral wound on the core between the core ends to form a second coil, the turns of the first and second coils being side-by-side in a single layer extending along the core, the ends of the second coil being uninsulated and wound over the single layer to form a second pair of electrodes at opposite ends of the core and spaced apart from the respective first electrodes.

4. The assembly defined in claim 3 wherein the core has holes extending laterally therethrough to provide anchors for the wire ends.

5. The assembly defined in claim 4 wherein the spacers are sealingly formed over the wire-end holes.

6. The assembly defined in claim 3 wherein the core is a hollow tube with an open distal end, and further comprising a connector assembly having a passage to receive one end of the electrode assembly, the connector assembly having connecting screws threaded therein into contact with the underlying electrodes of said one end.

7. A nerve-stimulating electrode assembly for delivering stimulating signals through body fluid to spinal nerves within the lower end of the vertebral column, comprising:
    a slender, elongated core having an inner end for insertion adjacent nerves to be stimulated, and an outer end for connection to a source of electrical signals, the core having a recess adjacent the inner end;
    an electrode disposed around the core in the recess;
    means for enabling charge injection through body fluid to a group of nerves, while deterring direct electrode contact with a nerve surface, said enabling means comprising radially extending portions of the core on opposite sides of the electrode, said portions being larger in outside dimension than the electrode to provide a space between the electrode and surrounding nerves for body fluid, and to deter electrode-nerve contact; and means for electrically connecting the electrode to the outer end of the core.

8. The assembly defined in claim 7 wherein the core has a plurality of spaced-apart recesses adjacent the inner end, each recess carrying an electrode disposed beneath the outer surface of the surrounding core, each electrode extending and being exposed substantially entirely around the core, and being electrically connected to the outer end of the core.

9. The assembly defined in claim 8 wherein the core is a hollow tube.

10. The assembly defined in claim 9 wherein the electrodes are made of material selected from the group consisting of iridium and platinum-iridium alloy.

* * * * *